United States Patent
Ray

(10) Patent No.: US 7,485,120 B2
(45) Date of Patent: Feb. 3, 2009

(54) TAPERED BONE FUSION CAGES OR BLOCKS, IMPLANTATION MEANS AND METHOD

(76) Inventor: Charles D. Ray, 4320 Via Presada, Santa Barbara, CA (US) 93110

( * ) Notice: Subject to any disclaimer, the term of this patent is extended or adjusted under 35 U.S.C. 154(b) by 62 days.

(21) Appl. No.: 11/025,217

(22) Filed: Dec. 29, 2004

(65) Prior Publication Data

US 2005/0159756 A1 Jul. 21, 2005

Related U.S. Application Data

(60) Provisional application No. 60/533,622, filed on Dec. 31, 2003.

(51) Int. Cl.
*A61B 17/56* (2006.01)
*A61F 2/46* (2006.01)

(52) U.S. Cl. ............... 606/87; 606/60; 606/90; 606/96; 606/99

(58) Field of Classification Search .......... 606/99, 606/57, 63, 105, 61, 60, 87, 90, 96
See application file for complete search history.

(56) References Cited

U.S. PATENT DOCUMENTS

| | | | | |
|---|---|---|---|---|
| 2,697,433 | A * | 12/1954 | Zehnder | 606/96 |
| 3,486,505 | A * | 12/1969 | Morrison | 606/90 |
| 4,730,616 | A * | 3/1988 | Frisbie et al. | 606/108 |
| 4,907,577 | A * | 3/1990 | Wu | 606/87 |
| 5,263,953 | A | 11/1993 | Bagby | |
| 5,385,567 | A * | 1/1995 | Goble | 606/96 |
| 5,409,489 | A * | 4/1995 | Sioufi | 606/80 |
| 5,431,658 | A * | 7/1995 | Moskovich | 606/99 |
| 5,531,751 | A * | 7/1996 | Schultheiss et al. | 606/96 |
| 5,676,666 | A * | 10/1997 | Oxland et al. | 606/61 |
| 5,797,909 | A | 8/1998 | Michelson | |
| 6,342,057 | B1 * | 1/2002 | Brace et al. | 606/96 |
| 6,436,119 | B1 * | 8/2002 | Erb et al. | 606/198 |
| 6,478,800 | B1 * | 11/2002 | Fraser et al. | 606/99 |
| 6,652,533 | B2 * | 11/2003 | O'Neil | 606/100 |
| 2002/0116062 | A1 | 8/2002 | Jackson | |
| 2002/0193881 | A1 | 12/2002 | Shapiro et al. | |
| 2005/0256578 | A1 * | 11/2005 | Blatt et al. | 623/17.15 |

OTHER PUBLICATIONS

PCT Search Report (mailed Feb. 8, 2006) (3 pgs.)

* cited by examiner

*Primary Examiner*—David H Willse
*Assistant Examiner*—Javier G Blanco
(74) *Attorney, Agent, or Firm*—Dicke, Billig & Czaja, PLLC

(57) ABSTRACT

A novel device and method for fusions inside a forward widely tapering human disc space. A stabilizing/guiding system is driven into and against the disc space. The device is further stabilized by spreading and gripping means inside both vertebral end plates. Rod retaining members hold calibrated rod units whose adapted tips perform reaming and threading of the disc space. Subsequently, the tapered cage or implant can be inserted by a free-hand method under direct vision into the prepared and tapered bed. Rod unit divergent angulation is preferably set to match that of the disc space as well as the implants so they obtain optimal distributed purchase of vertebral bone. In one embodiment, inserts are confluent with parallel medial walls rather than their long axes, increasing torsional or lateral translational stability and simplifying placement of additional bone chips. No tubular guide means are required.

19 Claims, 3 Drawing Sheets

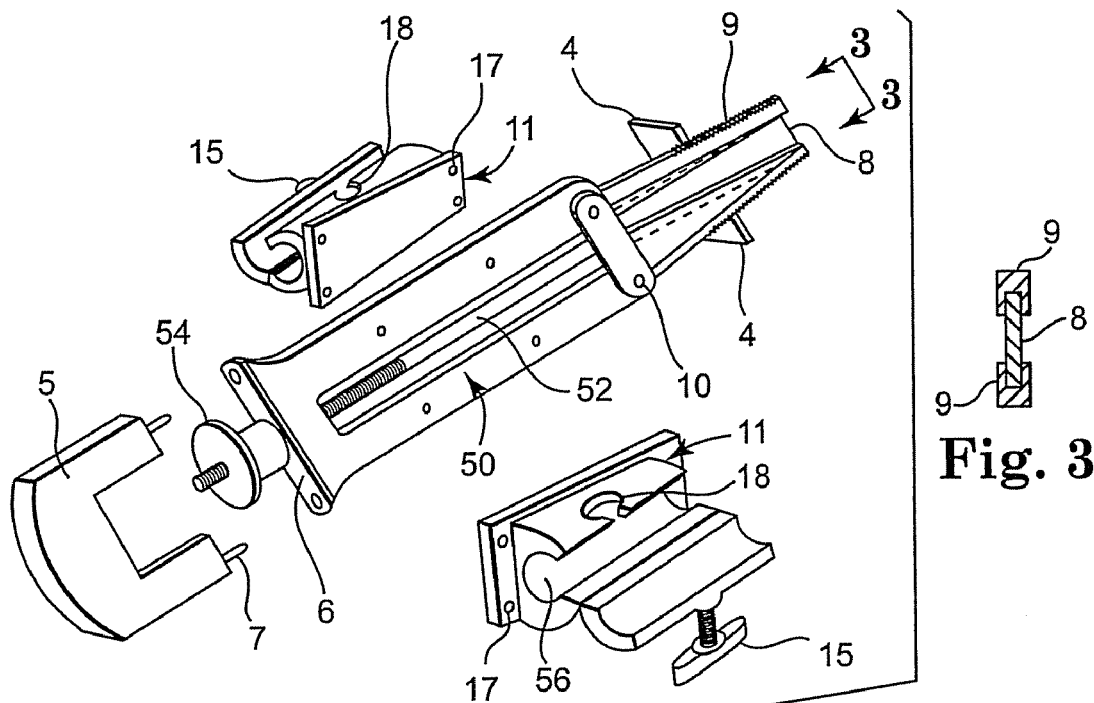
Fig. 3
Fig. 2
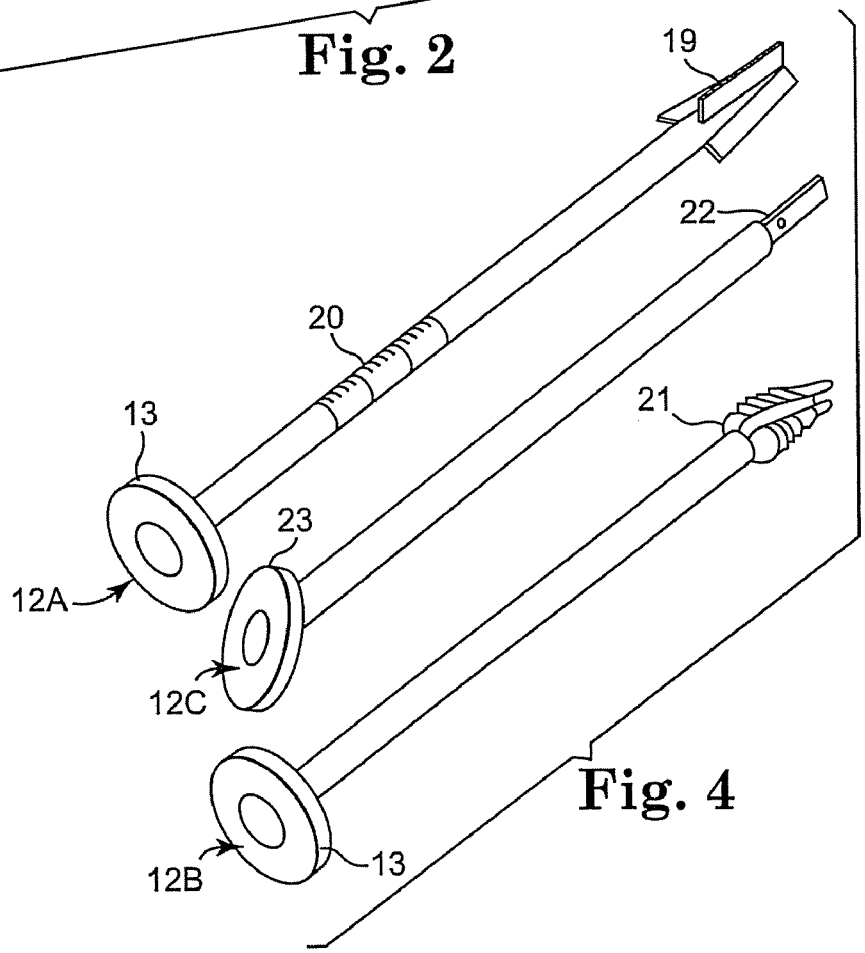
Fig. 4

TAPERED BONE FUSION CAGES OR BLOCKS, IMPLANTATION MEANS AND METHOD

CROSS-REFERENCE TO RELATED APPLICATIONS

This application claims the benefit of U.S. Provisional Patent Application Ser. No. 60/533,622, filed Dec. 31, 2003 and entitled "Tapered Bone; Fusion Cages or Blocks, Implantation Means and Method", the teachings of which are incorporated herein in its entirety.

BACKGROUND

The present invention relates to fusions of the spine, more specifically to intradiscal or interbody fusions utilizing hollow, formed, perforated, threaded cages in severe, disabling discogenic back pain problems, with or without a herniation (protrusion) of the disc.

Degenerative changes of the human spinal column often are accompanied by severe, disabling back pain; one method of success in eliminating such pain originating from within the disc, called discogenic pain, is to surgically eliminate the disc and create a fusion or bony union between adjacent vertebrae, eliminating the offending, painful disc. Several successful surgical devices and methods are now available to obtain the desired bone or suitable substitute fusion. One such valid method utilizes fusion cages that are hollow, usually threaded devices, to contain and protect the bone graft material; the cage is driven or screwed into the prepared disc space to facilitate the development of a solid bony fusion. Into these cages morcelized bone graft or substitute fusion inducing material is placed with the fusion developing by a growth of the contained material from one vertebra, through the multiple perforations in the cage walls, into the adjacent vertebra. Such devices are nearly all cylindrical with parallel walls; however, at some disc spaces having a forward-opening taper, it is preferable to use inserts having the same taper so they will more closely conform to that disc space taper and provide an improved distributed attachment of the insert along essentially all of the tapering disc space. Further, tightness of the laminated, circumferential collagen fibers of the annulus, the outer part of the flexible disc structure, is essential for early stability of the movable spinal segment. Thus, the goal is to immediately stabilize the segment by the implant while the fusion slowly develops. The device or material used to facilitate a fusion formation must initially be able to support the vertical forces, roughly up to 1.8 times the body weight and to induce or conduct the fusion formation.

The threaded fusion cage system was designed to simplify the surgery for spine fusion. Each cage of the pair ordinarily used in the procedure is inserted into the surgically prepared and tapped or threaded hole formed between the two adjacent vertebrae, penetrating into the bone of each. Although shaped bone grafts or substitute material may be used instead of the cages to accomplish the fusion in many cases, the cages permit the use of disorganized bone chips being held into position by the cage structure. The optimal penetration, called purchase, of each cage into each of the opposing vertebral bodies to be united by bone growth, known as a fusion process, has led to substantial success in fusing the spine for over 14 years and cages of various manufactures have been implanted in perhaps 500,000 patients worldwide. Cages are hollow threaded titanium devices nearly always formed as straight non-tapering cylinders and are appropriate for most applications since the end plates of the vertebral bodies are generally quite parallel.

Anatomically, however, some of the disc spaces are not parallel, particularly at the lowest lumbar space which adjoins the top of the sacrum bone. This space, called Lumbar 5-Sacral 1 (or L5-S1) is commonly involved in the disabling, degenerative discogenic pain process. The L5-S1 disc space normally has a taper, with a larger opening at the front. When parallel-walled fusion cages are inserted into the L5-S1 disc space, more commonly from a frontal or anterior approach through the abdomen, sections of the usual parallel walled cages maybe too deeply purchased towards the posterior portion of the disc space and essentially have little or no purchase into the more anterior or frontal portion of the tapering disc space. One solution to this problem to obtain good purchase along the majority of the disc space is to use a tapered fusion cage whose angle of taper is chosen to more closely match the forwardly widening angle of the disc. To suit a variety of anatomical variations, a range of tapering angles of cages is needed, usually 6°, 9° and 12°, larger towards the front. In addition, with this normally greater forward opening of the taper, it is extremely unlikely that it would be practical or safe (relative to posterior nerve issues) to utilize a posterior approach for implantation. Various tapered cage designs and methods of implant are described in Ray C. D, Dickhudt E. A: V-threaded fusion cage and method of fusing a joint. U.S. Pat. No. 4,961,740; and, Ray C. D, Dickhudt E. A: Surgical method and apparatus for fusing adjacent bone structures. U.S. Pat. No. 5,026,373; and Ray C. D: Surgically implanting threaded fusion cages between adjacent low-back vertebrae by an anterior approach. U.S. Pat. No. 5,05.5,X04; and Ray C. D: Instrumentation and method for facilitating insertion of spinal implant. U.S. Pat. No. 6,042,582; and Winslow C. J, Mitchell S. T, Jayne K, Ray C. D: Open posterior lumbar fusion cage insertion set and method. U.S. Pat. No. 6,083,225 Systems presently manufactured by Stryker Spine, Inc., of Allendale, N.J., as the Ray Threaded Fusion Cage and associate instruments are also instructive. Additionally, other tapered cage systems have been allowed U.S. patent coverage by other inventors.

Related Art—in the past various instruments and methods have been developed for anterior insertion of various appropriately shaped supportive materials that can induce or conduct the formation of a solid fusion. Such materials have included solid bone autografts (the patient's own shaped bone) or allografts (shaped cadaver bone), shaped artificial bone substitutes (bioceramics or ocean coral) or a variety of appropriately shaped cage-like devices, each of which is cut or formed to match the desired angle of forward taper. The greatest problems associated with the instrumentation used for the implantation of these materials or devices to be implanted have been: (1) rigidly attaching a guiding assembly (usually tubular) onto or within the disc space of adjacent vertebrae for subsequent preparation of the bed and subsequent insertion of the appropriately tapered devices or cages while maintaining the proper spacing (for a plurality of implants) and angulation of the devices to be used, (2) reaming (tapered drilling) the recipient bed while rigidly maintaining the direction and depth of this process, creating the appropriate recipient bed, (3) tapping the recipient bed, or utilizing self-tapping cages, while maintaining the same initial angulation and spacing used in the above earlier stages, and (4) appropriate tightening of the circumferential fibers of the annulus with stabilization of the operated segment through a means to expand the disc. For such procedures, most commonly utilized is an essentially tubular guiding means through which the preparation and steps of implantation are performed. Such tubular means are temporarily attached across or within the disc space. This tubular means, usually a singular or double-barreled device, is forcefully driven onto or into the disc space. Through this stabile tubular device, the bed for the paired cage is formed by boring or reaming, then the tapping, and followed by cage or device insertion. Subsequently or prior to insertion, the utilized cages are filled with appropriate bone chips or substitute. Importantly, all such procedures place the tapered cages or materials with their long axes parallel to each other. Since the disc space and matching angulated cages are larger in front, and after insertion may even touch, the placement of ancillary bone outside and between the implants, as many surgeons prefer, is inhibited. Further, because the overall width of the two adjacent implants is twice their diameters, the pair of implants may be excessively wide for that disc space.

SUMMARY

The novel system in accordance with one embodiment utilizes a variety of related instruments. Following adequate anterior lumbar transabdominal surgical approach and preparation of the affected disc space, including the scraping of end plate cartilages away from the adjacent vertebral bodies, a rod stabilizing/guiding instrument is driven into the disc space using a hammer striking against a removable plate. The guide has means to expand vertically to appropriately tighten its grip inside the tapering disc space while minimally changing the disc taper angle, by its expanding/lifting upper and lower knurled surfaces engaging the end plates along the majority length of their angulated central disc space surfaces. Each desired angulation, preferably 6°, 9° or 12° has a set of reaming or boring, threading or tapping instruments coded for ease in matching their various angulated components. The stabilizer/guide of this novel set of instruments is adjustable to accommodate various disc taper angles. Once the guide device is driven and stabilized inside the disc space and tightened, appropriately guided ancillary rod-mounted instruments are used to ream and tap for the later insertion of suitable tapered cages with great precision. These rod-mounted components pass through lateral guiding members, fixably removable and changeable as the procedure progresses. These rod guiding members are appropriately marked as to depth of penetration into the disc space. At conclusion of the prepared threaded recipient bed, the stabilizing/guiding unit is unlocked and removed from the vertebrae. The tapered insert is attached to the insertion rod and following the visible tapped recipient bed, screwed into position freehand under direct observation and by intraoperative fluoroscopy, a technique familiar to skilled surgeons such as is performed routinely in the insertion of pedicle screws and the like. When a prepared cage with arcs cut into the outer sides is used, it is implanted as first of the pair where the second may or may not have such side cuts. The pair of cages will this be nestled closer together, with a narrower total width, than if cages with no such side cut arcs were used. Since the insert is tapered, the disc space does not require a support to keep it open after the guide unit is removed; the taper will reopen the disc according to the depth of insertion of the tapered insert. Additional bone may be packed posterior and lateral to the cages.

BRIEF DESCRIPTION OF THE DRAWINGS

FIG. 2 is a perspective, exploded view of a portion of the system of FIG. 1;

FIG. 3 is a cross-sectional view of the system of FIG. 2;

FIG. 4 is a perspective view of various rods useful with the system of FIG. 1;

DETAILED DESCRIPTION OF THE PREFERRED EMBODIMENTS

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
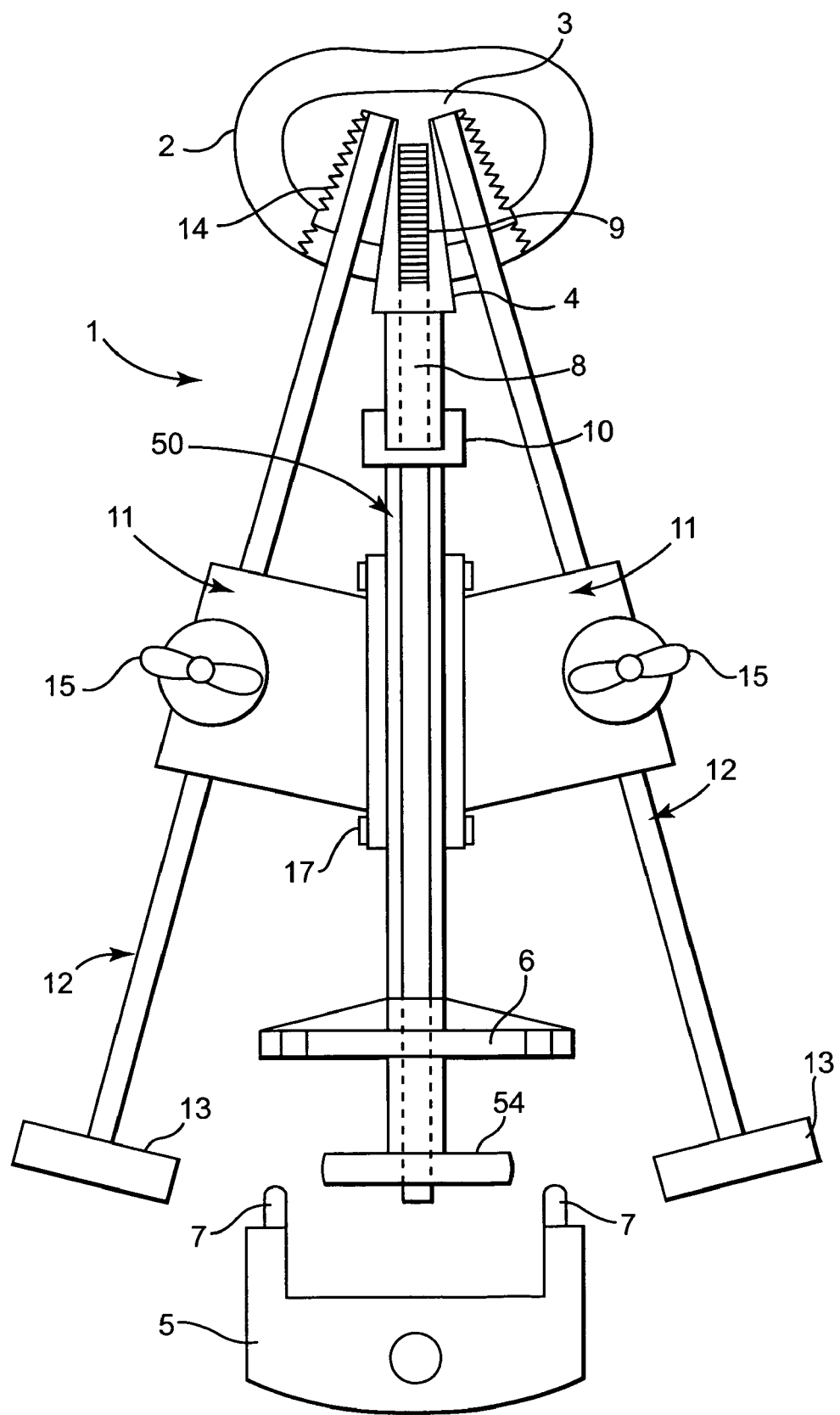
FIG. 1 is a simplified, top plan view of a system for implanting tapered spinal fusion cages or similar devices in accordance with the present invention in conjunction with a spinal disc space.

FIG. 1 is a composite, diagrammatic plan view from above showing one embodiment of a stabilizing/guiding system 1 in accordance with the present invention engaged against the anterior aspect of a vertebra 2 and a portion extending inside a vertebral disc space 3 with tabs 4 firmly against the anterior aspect of the vertebrae 2, along with a generic representation of a tapered cage 14. In general terms, and with additional reference to FIG. 2, the system 1 includes a guide body 50 defining a proximal surface 6 and a distal end forming tabs 4 and stabilizer tips 9 that are pivotable about a corresponding hinge point 10 via interface with a wedge or similar device 8. Movement of the wedge 8 is dictated by a central drive body 52 (e.g., a shaft) otherwise proximally accessible via a knob 54. In addition, the system 1 includes opposing lateral guide or rod retaining members 11 attached to the guide body 50. The lateral guide members 11 are, in one embodiment, releasably secured to the guide body 50 by a plate 17. Further, each of the lateral guide members 11 defines a selectively accessible passage 56 adapted to selectively receive and maintain a rod unit 12 via, for example, a winged knob 15 secured within a socket 18. The rod unit 12 is described in greater detail below with reference to FIG. 4, but generally includes a distal, working end and a proximal knob 13 or similar structure. During use, the system 1 is driven into the surgically prepared disc space 3 using a hammer (not shown) struck against a removable striking block 5 which is temporarily positioned against the proximal surface 6 by indexing pins (7).

After driving the system 1 against the vertebrae 2, the striking block 5 is removed and the tightening knob 54 is rotated which pulls the wedge or other means 8 inside the knurled stabilizer tips (9) causing their knurled surface to be temporarily imbedded into the opposing walls of the vertebral end plates (not shown). The knurled stabilizer tips 9 are hinged 10 so they may spread apart inside the disc space 3. The lateral guide or rod retaining members 11 for guidance of rod units 12 having suitable knobs 13 for hand drilling or reaming, tapping or threading of the bed for later free hand cage 14 insertion is thus under firm and repeatable control. The lateral guide members 11 are opened for changing the rod units 12 then firmly held in proper position using winged knobs 15, or similar means, as needed to drill or ream the recipient bone bed, thread or tap the bed and provide the suitable bed for subsequent freehand implantation of the suitable tapered cages 14. The angulation 16 of the lateral guide members 11 relative to the midline is selected and fixably alterable to be the same as the angulation of the tapered cages 14. The lateral guide members 11 are removably attached to the guide body 50. A hinged screw 15 on the lateral guide member 11 fits into the rounded socket 18 and held firmly by means such as winged knobs 15. The adjoining surfaces of the subsequently implanted, paired cages 14 are closely paralleled to each other.

FIG. 2 is a diagrammatic perspective view seen laterally of the stabilizing/guiding system or unit 1 and associated components. As shown in FIG. 1, the long axis of the system 1 is driven into the surgically prepared disc space 3 until the tabs 4 engage the anterior vertebral margins, utilizing the block 5 removably attached to the end 6 by index pins 7. After firmly seating the stabilizing/guiding system 1, the striking block 15 is removed and the fixation knob 54 is rotated pulling the wedge 8 or suitable means inside the knurled stabilizer tips 9, hinged 10 on the stabilization/guiding system 1, thus firmly anchoring the deep end of the unit tips 9 inside the disc space 3 and maximally opening and tightening the fibers of the circumferential, ligamentous vertebral annulus (unnumbered). The angulated lateral guide members 11 are opened laterally for placement of the rod units 12 for drilling (reaming) and tapping (threading) to prepare the recipient bed for subsequent insertion of cages 14. The lateral guide members 11 are removably attached to the stabilization/guiding unit 1 by suitable means such as screws (not shown). The tapered half-sockets 18 are shown where the bases of the screws with winged knobs are seated when tightened.

FIG. 3 is a diagrammatic cross-section showing the wedge 8 inside the knurled tips 9 of the stabilizing/guiding unit 1 and the cages (not shown), one with arcuate lateral cuts, are closely approximated.

FIG. 4 is a composite diagram of the two rod units 12 for drilling (reaming) A, tapping (threading) B, and the separate rod later used for subsequent free hand cage insertion C. Each rod unit 12 is hand torqued using its knob 13. Each rod 12 unit is calibrated in millimeter/centimeter increments 20 as referenced to the outer margin of the lateral guide member 11 (FIG. 2) to indicate the depth of reaming or tapping. Each rod unit 12 is changeably removable from the lateral guiding member 11 as needed without disturbing the stability or guidance of the main unit. The "A" rod unit 12A has an odd plurality of sharp flat cutting (reaming) vanes 19, usually three, where the odd number provides a more uniform torque on reaming between the parallel vertebral end plate surfaces than would be obtained if the reamer used an even number of vanes. The vanes 19 may also be slightly spiraled for even more uniform torque and spontaneous removal of debris. The tapping rod unit 12B has an odd fluted spiraled tap 21 for even torque on tapping the reamed hole. The subsequently freehand cage insertion rod unit 12C has a suitable engaging means 22 to removably connect a cage mounted on its tip. A ball detent or similar means serves to removably retain the cage (not shown) until it is firmly installed. The handle of this rod unit 12C is oval with directional markings to indicate the position of the potentially arcuate side cuts of cages, if they are provided, that must face the full cage. The insertion rod unit 12C, or similar insertion device, can be used apart from the system 1 (e.g., freehand, with the system 1 removed from the disc space 3), or with the system 1 still in place.

Figures 5, 6:
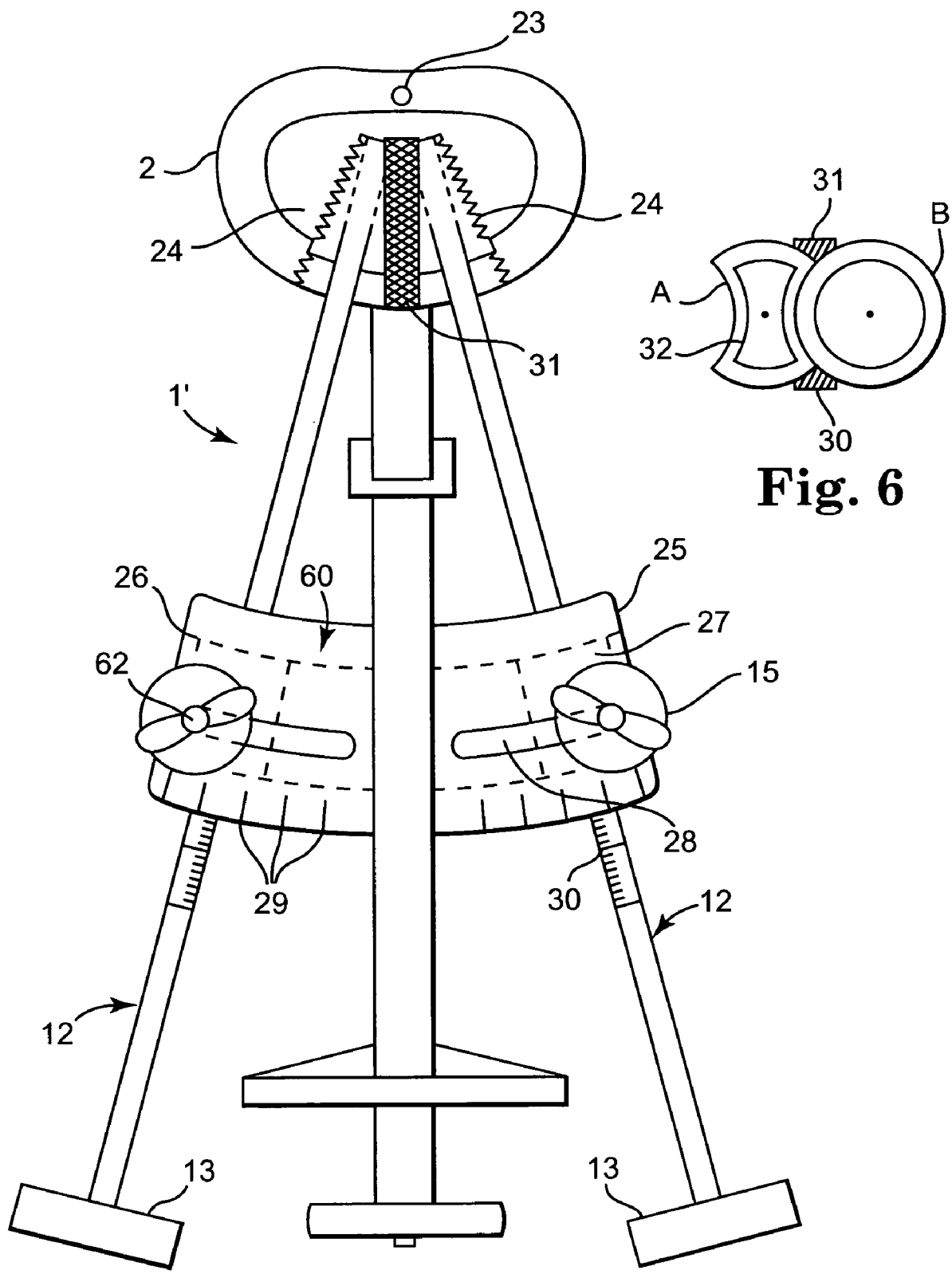
FIG. 5 is a simplified, top plan view of an alternative embodiment system in accordance with the present invention.
FIG. 6 is an enlarged, cross-sectional view of two tapered fusion cages following implant using the system and method of the present invention.

FIG. 5 is a composite, diagrammatic plan view of an alternative embodiment stabilizing/guiding system 1' closely reflecting major details of FIG. 1. The system 1' is adapted to selectively retain rod units 12 (FIG. 1), such as rod units for reaming 12A (FIG. 4), tapping 12B (FIG. 4), and subsequent free-hand insertion 12C (FIG. 4) of the tapered cages 14, 24. To this end, the system 1' is adapted to direct the rods 12 towards a virtual confluent or hinge point 23 near the distal margin of the vertebral bodies 2. Maintenance of correct angulation for implantation of tapered cages, determined by the angular opening of the disc space between the adjacent vertebral bodies, matched with tapered cage angulation, is determined by rod attachment member 60 having a sector plate 25 and adjustable components having the same virtual hinge point 23.

The sector plate 25 has a flat upper surface and a keystone mortised under surface 26 into which a sliding guide 27 closely and fixably fits. The sliding guide 27 is adapted to receive one of the rods units 12. The upper surface of the sector plate 25 has a curving slot 28 through which a screw 62 provided with the rod attachment member 60 passes to be movably fixated at a desired position by tightening a wing nut 15. This fixation simultaneously fixates the sliding guide 27, and thus the associated rod unit. Markings 29 on the sector plate 25 denote the chosen angulation. Markings 30 on the rod units 12 indicate the depth of penetration into the disc space by their tip structures.

FIG. 6 is a diagrammatic cross-sectional view of two, implanted Stryker Spine, Inc. Ray 'Unite'™ tapered fusion cages. The elevating and fixating spreader tips 31 having knurled outer surfaces associated with the stabilizing/guiding unit of the present invention are adjusted to accommodate the contour of the appropriate tapered cages. In the Unite cage implantation version, the first implanted of the pair, cage A has relieved medial walls 32 one on each side, 180° apart, against either of which the second cage B with a standard wall closely fits. Two 'Unite' or similar cages (having arcuate side cuts) may also be used. This configuration permits a closer proximity of the centers of the two cages and a reduced overall width of the combined implants than would be permitted by two fully cylindrical cages.

The structure of the principal stabilizing/guiding unit or system of the present invention may be constructed essentially oval in cross section as well as essentially flat as shown. Depending on the width of the surgical approach and the depth to the target vertebrae, varying with the obesity of the patient's abdomen, various implantation/guidance units may be of different size or may be constructed with length telescoping/expanding capability. Other variations may include torque knob design, internal low friction bearing surfaces of the lateral guiding members or methods of attachment of these members to the main unit as well as variations in means of closure of the guiding surface halves of these members. Design of the cages may be simple tapered adaptations of the present Ray threaded fusion cages, similar to considerably smaller, tapered ones now manufactured by Stryker Spine for fusions of the cervical spine (neck).

EXAMPLE AND METHOD OF USE

A suitable patient having discogenic, painful degenerative disc disease is examined using x ray techniques and on finding that the angulation between the particular vertebral end plates is 6 degrees or greater, the surgeon may decide-to use tapered rather than parallel cylindrical cages for his patient. If the segment to be operated is at L5-S1 (the usual one), the surgeon then notes the anatomical position of the top of the symphysis pubis, where the pelvis joins at the front of the body. He then draws a line through the middle of the disc to be operated extending it in the direction of the symphysis. If this line extends below the top of the symphysis, it indicates that the stabilizing/guiding unit may be too large, vertically, and therefore not usable on this patient. This means that the angle of taper as well as the segment tilt angle through the disc centrum relative to the symphysis are both important in patient selection. In some patients the tilt angle is so vertically severe that an anterior approach to the L5-S1 disc space may not be possible. Fortunately, this situation is quite uncommon.

The appropriate tapered cages or suitable insert and associated instruments are chosen and made ready. The patient is anesthetized and appropriately positioned, the abdomen is prepared with an exposure usually via a retroperitoneal dissection (moving the abdominal organs from the patient's left to the right side, along with the intact peritoneal sac). The abdominal exposure must be wide enough to accommodate the angulation of the rods used in the procedure to ream, tap and then insert. The major anterior vessels and other important structures are mobilized and handled as for any routine anterior retroperitoneal fusion approach, a common technique during anterior spinal fusion procedures. The anterior annulus is removed sufficient only to accommodate the width of the pair of cages or inserts; the entire cartilage of the end plates is scraped away down to bleeding bone but not to penetrate the bone of the end plates. The stabilizing/guiding unit is driven into position against the anterior aspect of the vertebra and its locking tip is expanded to fully stabilize the unit and this stability is evaluated by moving the unit in several planes, showing that the two vertebrae and the unit move essentially as though a single structure. The reaming and tapping into the disc space as indicated above. The guide unit is removed and the tapered cage is inserted free hand using its rod, carefully inserting the first arcuate side cut cage then the fully round one. The final positioning of the cage pair is demonstrated by intraoperative x-ray fluoroscopy then the cages are filled with morsels of bone or substitute and the procedure finished by routine closure of the tissue layers and the skin incision. In that the procedure closely parallels common anterior fusions, patients should respond quite well to the procedure and post-operative care. Patients ordinarily wear a corset but in some cases a rigid brace may be needed for a few months. Subsequent office visits should include repeat x-rays to determine the progress of the fusion and if any displacements or other problems have arisen before the fusion becomes fully solid (in about 3-5 months).

Advantages

The invention has the novel ability to utilize a pair of fusion cages or suitable material blocks having The selected angulation of taper to, match the tapering angles found in several patients having disabling discogenic pain and disc degeneration, particularly at the L5-S1 space. The divergent angulation of the approach to insert the cages or blocks of material being the same as the actual taper angle of the disc space permits the facing or medial edges of the implants inside the disc space to be parallel along their lengths, uniquely improving the availability of surrounding disc space for a narrower overall width of the implant pair plus additional bone graft placement. The angulation of the set of appropriate instruments and the cage pair to be used is determined preoperatively and the overall procedure is uniquely well controlled by the means of central stabilization of the disc space and the ancillary guidance components. The stabilizing/guiding unit firmly controls the approach angle bilaterally throughout the procedure without slipping or dislocation assuring excellent matching of the steps of the procedure and therefore the overall fusion rate and success. Further, the vertical opening or expansion of the knurled fixation member is placed at or close to its virtual disc center of flexion/extension motion of the disc and therefore on distraction, elevation and tightening of the circumferential annuls fibers, the taper angle is largely unchanged. If the disc space is tilted laterally, as in cases with localized scoliosis, the taper angle is generally the same but the height of the disc space is different on the two sides. By inserting the tapered cage of block more or less into the depths of the disc space, thus difference in height can be adjusted or even corrected; not possible when using straight cylindrical cage implants. Therefore, the require accuracy of the implantation is controlled throughout the reaming and threading steps of the procedure in preparation for the final direct visual free-hand insertion of the tapered cages, all of which expectedly will improve on the overall results where occasional surgical problems have arisen from other instrument methods not so well controlled. Since the entire procedure is as well under direct vision by the surgeon, the steps are better controlled than with implantation techniques utilizing essentially blinded tubular guides for each stage from the reaming to the insertion. Lastly, the angulation for the final position of the implants has a confluent and not parallel insertion path, there should be an improvement in the rotary and lateral translocation stability of the final result.

The novel system places the tapered cages or fusion inducing devices material with their long axes convergent posteriorly where the convergent angle is the same as the taper angle of the disc space. Therefore, the cages come close together at a constant distance between them, throughout their lengths. Cages machined with arcs cut from one or more outer surfaces equal to their circumferential contour permit them to be brought into close contact at a width less than the combined diameters, throughout their lengths. At the deep converging tip of the implants, sufficient width within the vertebrae remains so additional graft material can be placed, as may be desired by the surgeon. Additionally, with the cage's long axes nested together, the disc is more stable against lateral translocation or "side roll". The depth of insertion of the tapered implants is useful to wedge tighten the annular fibers, promoting immediate stability over parallel walled implants. The novel system stably achieves the boring or reaming and tapping in preparation for cage insertion quite accurately, utilizing a rod alignment/guiding instrument and attachments. A tubular guide unit is not employed for any of these steps and the common rod guidance is utilized only for the boring or reaming and threading or tapping steps. That is, once the reaming or boring and tapping are performed, the guiding assembly is removed and the insertion of cages installed by hand into the provided appropriately oriented and tapered cavities. The angulation and orientation for boring and tapping provided by the adjustable long rod/guide assembly are selected and fixed according to the required taper angle of the disc space and selected cage implant. Further, prior to attachment of the guiding/stabilizing assembly, the deep central disc space may be prepared laterally into the vertebral bone for ancillary bone placement outside the anticipated confluence of the cage tips. The fixed (static) and opening up or spinal extension position (dynamic) tapering angles which the implants should closely match are determined in advance of the surgery utilizing lateral x-ray views of the lumbar spine in neutral, forward flexion and reverse extension positions. In addition to determining the taper angle of the disc space, this maneuver aids in assessing the flexibility of the space. That is, the more flexible the disc the more it will open on extension and the greater the cage taper angle that may be needed following the attachment of the stabilizing/guiding assembly. The novel stabilizing/guiding instrument is adjustable to the same angular taper as the implants to be used, primarily 6°, 9° or 12° or other suitable angle as indicated. Those skilled in these arts may provide other means for adjustment of the guiding instrument to suit various taper angles, in addition to the rod assembly herewith disclosed without departing from the intent and novelty of this document system.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A system for implanting a pair of fusion cages or similar fusion-inducing devices into a spinal disc space, the system comprising:
    a guide body defining a proximal end, a distal end adapted for engagement with the disc space, and a central axis extending through the proximal and distal ends; and
    first and second rod retaining members positioned at opposite sides of the guide body, respectively, each defining a guide axis and adapted to selectively retain a rod unit, respectively, along the corresponding guide axis, wherein the guide axes are aligned along a transverse plane;
    wherein the guide axes and the central axis are co-planar, and the guide axes are angularly positioned relative to the central axis such that the guide axes intersect the central axis adjacent and distal the distal end of the guide body and extend in a laterally spaced manner relative to corresponding sides of the distal end,
    wherein the proximal end of the guide body is proximal the rod retaining members, and the distal end of the guide body is distal the rod retaining members, and further wherein the distal end of the guide body includes an expandable tip, which expandable tip is expandable only in a direction perpendicular to the transverse plane.

2. The system of claim 1, wherein a lateral distance between the guide axes and the central axis increases proximal the distal end of the guide body.

3. The system of claim 1, wherein the rod units comprises:
    a first rod unit selectively retained by the first rod retaining member; and
    a second rod unit selectively retained by the second rod retaining member.

4. The system of claim 3, wherein the rod units are selected from the group consisting of a reaming rod unit, a tapping rod unit, and an insertion rod unit.

5. The system of claim 3, wherein each rod unit includes a rod terminating in a distal, working end, and further wherein the rod includes index markings along a length thereof.

6. The system of claim 1, wherein the rod retaining members are configured such that an angular orientation of the respective guide axes relative to the central axis is adjustable.

7. The system of claim 6, wherein the rod retaining members each include a guide piece defining the guide axis and slidably connected to a support plate secured to the guide body.

8. The system of claim 1, wherein the expandable tip includes opposing tip bodies adapted to engage an intervertebral end plate.

9. The system of claim 8, wherein the guide body further includes a shaft operably connected to the opposing tip bodies such that movement of the shaft selectively causes expansion of the tip bodies relative to one another.

10. The system of claim 9, wherein the shaft terminates in a distal wedge slidably positionable between the opposing tip bodies.

11. The system of claim 1, further comprising a striking block removably assembled to the proximal end of the guide body.

12. The system of claim 1, wherein the first rod retaining member is configured to selectively define a longitudinal passage, a first state in which a rod unit is retained in the longitudinal passage, and a second state in which a rod unit is removable from the longitudinal passage, and further wherein a radial opening to the longitudinal passage is greater in the second state than in the first state.

13. A system for implanting a pair of fusion cages or similar fusion-inducing devices into a spinal disc space, the system comprising:
    a guide body defining a central axis, a proximal end, and a distal end including an expandable tip adapted for engagement with the disc space;
    first and second rod retaining members positioned at opposite sides of the guide body, respectively, each of the rod retaining members defining a guide axis, wherein the guide axes are aligned along a transverse plane;
    wherein the guide axes are angularly positioned relative to the central axis such that the guide axes intersect the central axis distal the expandable tip; and
    first and second rod units provided apart from the guide body and selectively retained by a respective one of the rod retaining members, each of the rod units terminating in a working end;
    wherein upon final assembly, the rod units are selectively positionable such that the respective working ends extend distally beyond the corresponding rod retaining member, and further wherein the system is configured such that the expandable tip is expandable only in a direction perpendicular to the transverse plane.

14. The system of claim 13, wherein the guide axes and the central axis are co-planar.

15. The system of claim 13, further comprising:
    a striking block removably assembled to the guide body and configured to translate a user-applied force onto the proximal end of the guide body.

16. The system of claim 13, wherein the first rod retaining member is configured to define a first state in which the first rod unit is radially captured within a longitudinal passage defined by the first rod retaining member, and a second state in which the first rod unit freely moves radially into and from the longitudinal passage.

17. The system of claim 16, wherein the first rod retaining member includes a first longitudinal section and a second longitudinal section combining to define the longitudinal passage, the second longitudinal section being pivotally attached to the first longitudinal section.

18. The device of claim 17, wherein the first rod retaining member further includes a locking device for selectively locking the second longitudinal section to the first longitudinal section in the first state.

19. A system for implanting a pair of fusion cages or similar fusion-inducing devices into a spinal disc space, the system comprising:

a guide body defining a proximal end, a distal end adapted for engagement with the disc space, and a central axis extending through the proximal and distal ends, wherein the guide body includes:

opposing tip bodies at the distal end forming an expandable tip, a shaft operably connected to the opposing tip bodies such that movement of the shaft selectively causes expansion of the tip bodies relative to one another; and first and second rod retaining members positioned at opposite sides of the guide body, respectively, and each defining a guide axis;

wherein the guide axes and the central axis are co-planar, and the guide axes are angularly positioned relative to the central axis such that the guide axes intersect the central axis adjacent the distal end of the guide body and extend in a laterally spaced manner relative to corresponding sides of the distal end, and further wherein the proximal end of the guide body is proximal the rod retaining members and the distal end of the guide body is distal the rod retaining members.

* * * * *